US007850858B2

(12) United States Patent
Kobayashi et al.

(10) Patent No.: US 7,850,858 B2
(45) Date of Patent: Dec. 14, 2010

(54) GRANULOCYTE ADSORBENT

(75) Inventors: Akira Kobayashi, Hyogo (JP); Shinya Yoshida, Hyogo (JP); Hideo Niwa, Hyogo (JP)

(73) Assignee: Kaneka Corporation, Osaka (JP)

( * ) Notice: Subject to any disclaimer, the term of this patent is extended or adjusted under 35 U.S.C. 154(b) by 663 days.

(21) Appl. No.: 11/661,320

(22) PCT Filed: Aug. 30, 2005

(86) PCT No.: PCT/JP2005/015744

§ 371 (c)(1),
(2), (4) Date: Feb. 27, 2007

(87) PCT Pub. No.: WO2006/025371

PCT Pub. Date: Mar. 9, 2006

(65) Prior Publication Data

US 2008/0021365 A1 Jan. 24, 2008

(30) Foreign Application Priority Data

Aug. 30, 2004 (JP) ............................. 2004-250745
Mar. 28, 2005 (JP) ............................. 2005-091445

(51) Int. Cl.
B01D 37/00 (2006.01)
B01D 15/08 (2006.01)
B01D 39/00 (2006.01)

(52) U.S. Cl. .................... 210/767; 210/252; 210/500.3; 210/500.31; 210/500.42; 210/644

(58) Field of Classification Search ................ 210/644, 210/645, 650, 767, 252, 258, 500.3, 500.31, 210/500.42
See application file for complete search history.

(56) References Cited

U.S. PATENT DOCUMENTS

| 2,112,275 | A | * | 3/1938 | Dreyfus ......................... 8/130 |
| 2,642,420 | A | * | 6/1953 | Kenyon et al. ................ 525/62 |
| 4,255,267 | A | * | 3/1981 | Hoehn et al. ................. 210/678 |
| 4,330,410 | A | * | 5/1982 | Takenaka et al. ............ 210/767 |
| 5,567,443 | A | * | 10/1996 | Kashiwagi et al. .......... 424/529 |
| 5,725,768 | A | * | 3/1998 | Adachi et al. ............... 210/435 |
| 5,977,346 | A | * | 11/1999 | Saka et al. .................... 536/63 |
| 6,498,007 | B1 | * | 12/2002 | Adachi et al. ................. 435/5 |
| 6,878,269 | B2 | * | 4/2005 | Nanko et al. ................ 210/259 |
| 2002/0174490 | A1 | * | 11/2002 | Kim et al. .................. 8/115.51 |
| 2003/0152569 | A1 | * | 8/2003 | Sawada et al. ........... 424/140.1 |
| 2007/0068870 | A1 | * | 3/2007 | Johnson et al. ............. 210/645 |
| 2008/0021365 | A1 | * | 1/2008 | Kobayashi et al. ......... 604/6.03 |

FOREIGN PATENT DOCUMENTS

| JP | 02-193069 A | 7/1990 |
| JP | 2004-041373 A | 2/2004 |
| WO | WO 01/70820 A1 | 9/2001 |

OTHER PUBLICATIONS

Iryo Yogu Dai Yon Chosa Iinkai, et al.; online (www.jaame.or.jp/kanren/sin_iryo/9908kk3.html); Japan Association for the Advancement of Medical Equipment; Inspection Report; Fourth Inspection Committee on Medical Appliance; Jul. 13, 1999, Partial English Translation.

* cited by examiner

*Primary Examiner*—John Kim
(74) *Attorney, Agent, or Firm*—Sughrue Mion, PLLC

(57) ABSTRACT

This invention relates to a granulocyte adsorbent comprising a polymer compound having an unsubstituted hydroxyl group and a hydroxyl group in which H has been substituted with at least one substituent R, a method for producing such adsorbent, a device for adsorbing granulocytes and a system for removing granulocytes using such adsorbent, and body fluid or a cell suspension from which granulocytes have been removed using such adsorbent.

8 Claims, No Drawings

GRANULOCYTE ADSORBENT

TECHNICAL FIELD

The present invention relates to a granulocyte adsorbent for selectively removing granulocytes from body fluid by adsorption, a method for producing such adsorbent, a device for adsorbing granulocytes and a system for removing granulocytes using such adsorbent, and body fluid from which granulocytes have been removed using such adsorbent.

BACKGROUND ART

Needs for techniques for selectively separating cells from a patient's blood are increasing along with the development of cancer therapy or transfusion of cellular blood components, and particularly in light of the recent development of cellular medicine and regenerative medicine. Removal of granulocytes from blood is particularly important in order to suppress inflammation or graft-versus-host-disease (GVDH) after implantation. For example, the following techniques for separating granulocytes from blood have been disclosed in the past: specific gravity and density gradient centrifugation involving the use of a Ficoll or Percoll solution to separate cells based on differences in specific gravity of the cells; and a method involving the use of a material that is assumed to selectively adhere to granulocytes, such as polyester fibers, nylon fibers, or cotton (e.g., JP Patent Publication (kokai) Nos. 54-46812 A (1979) and 57-11920 A (1982)).

A specific gravity and density gradient centrifugation technique, however, still has many drawbacks. Examples include safety issues such as in regards to cytotoxicity of a density gradient solution; operability issues, such as the time required for operations such as centrifugation or washing, along with contamination resulting from operations in an open system; and low separation efficiency arising from contamination with lymphocytes. In contrast, a method for selectively adsorbing granulocytes is superior to methods involving specific gravity and density gradient centrifugation in terms of safety and operability since such technique can be carried out in a closed system. Also, modifications of contact areas, materials, configurations, and other conditions have been attempted in order to further improve separation efficiency.

JP Patent Publication (kokoku) No. 58-54126 B (1983) discloses a technique for increasing the surface area of a granulocyte adsorbent. However, this document describes that the adsorbent also adsorbs lymphocytes in addition to granulocytes. That is, increase in contact areas does not lead to the expression of granulocyte selectivity. JP Patent Publication (kokai) No. 2-193069 A (1990) discloses a method for selectively adsorbing granulocytes using granulocyte-adsorbing carriers that have higher affinity for granulocytes than for lymphocytes and can be used for determining changes in the pathological conditions of a cancer patient or for cancer treatment.

Such carriers comprise substances each having a contact angle with water of 55 to 95 degrees, and materials having high affinity for granulocytes, such as polystyrene, cellulose acetate, 6-nylon, and polyethylene terephthalate, are provided as examples. Also, a similar report has been made concerning the contact angle and the adhesion rate of neutrophils, which are major constituents of granulocytes (the 19th Biomedical Polymers Symposium abstracts, pp. 51 to 52, the Society of Polymer Sciences, Japan, Jun. 11, 1990). In such report, neutrophils are reported to have higher affinity for a material with which the contact angle of an adhesion substrate with water is approximately 70 degrees, and the influences of materials are reported to be significant in the expression of granulocyte selectivity.

JP Patent Publication (kokai) No. 5-168706 A (1993) discloses that adhesion of granulocytes is not associated with the contact angle of a given material and is defined by the surface roughness of the contact surface. Thus, it has been demonstrated that mere increase of contact area is not sufficient in order to express granulocyte selectivity. Factors such as the surface roughness of the adhesive substrate and hydrophilic or hydrophobic properties (the contact angle) are associated with the selectivity. With the use of a material with a modified contact angle or surface roughness, granulocyte selectivity is not always satisfactory. Accordingly, development of a granulocyte-separating material, a granulocyte-adsorbing apparatus, and a method with improved selectivity for granulocytes has been awaited.

Existing commercially available granulocyte-adsorbing columns or leukocyte-adsorbing columns have drawbacks in terms of body fluid compatibility; that is, platelet adhesion. Large quantities of platelets adhere to areas in the vicinity of column inlets, resulting in elevated blood pressure or lowered blood platelet concentration.

Patent Document 1: JP Patent Publication (kokai) No. 54-46812 A (1979)

Patent Document 2: JP Patent Publication (kokai) No. 57-11920 A (1982)

Patent Document 3: JP Patent Publication (kokoku) No. 58-54126 B (1983)

Patent Document 4: JP Patent Publication (kokai) No. 2-193069 A (1990)

Patent Document 5: JP Patent Publication (kokai) No. 5-168706 A (1993)

Non-Patent Document 1: The 19th Biomedical Polymers Symposium abstracts, pp. 51 to 52, the Society of Polymer Sciences, Japan, Jun. 11, 1990

DISCLOSURE OF THE INVENTION

The present invention provides a granulocyte adsorbent with enhanced efficiency in terms of selectively removing granulocytes, a method for producing such adsorbent, a granulocyte-adsorbing device using such adsorbent, and body fluid from which granulocytes have been removed using such adsorbent, none of which could be attained by the aforementioned conventional techniques.

The present invention also provides a granulocyte adsorbent used for extracorporeal circulation, which is capable of selectively removing granulocytes from body fluid by adsorption and has high body fluid compatibility (e.g., suppression of platelet adhesion), and a system for removing granulocytes using the same.

The present inventors have conducted concentrated studies concerning a polymer compound-compound conjugate, in which a hydroxyl-containing polymer compound reported to have affinity for granulocytes (e.g., cellulose acetate) is bound to another compound by a bond that is cleavable through contact with an alkaline solution. As a result, they discovered that removal of part of the aforementioned compound from the conjugate would realize significant improvement in specific affinity for granulocytes, compared with affinity for mononuclear cells including lymphocytes and monocytes. They also discovered that stabilized direct blood perfusion could be realized because of reduced interactions with platelets. Accordingly, the present invention provides the following.

(1) A granulocyte adsorbent comprising a polymer compound having an unsubstituted hydroxyl group and a hydroxyl group in which H has been substituted with at least one substituent R.

(2) The granulocyte adsorbent according to (1), wherein the polymer compound is polyvinyl alcohol, a polyvinyl alcohol copolymer, or a polysaccharide having an unsubstituted hydroxyl group and a hydroxyl group in which H has been substituted with at least one substituent R.

(3) The granulocyte adsorbent according to (1) or (2), wherein the substituent R is acyl.

(4) The granulocyte adsorbent according to any one of (1) to (3), which is insoluble in water.

(5) The granulocyte adsorbent according to any one of (1) to (4), wherein the percentage of hydroxyl groups substituted with substituent R is 35% to 53% among all hydroxyl groups.

(6) The granulocyte adsorbent according to (5), wherein the polymer compound is cellulose acetate in which the percentage of hydroxyl groups substituted with acetyl groups is 35% to 53% among all hydroxyl groups.

(7) A device comprising a container that contains the granulocyte adsorbent according to any one of (1) to (6).

(8) The device according to (7), wherein the container comprises an inlet and an outlet for liquid.

(9) The granulocyte adsorbent according to any one of (1) to (4) used for extracorporeal circulation.

(10) The granulocyte adsorbent according to (9), wherein the percentage of hydroxyl groups substituted with substituents R is 5% to 53% among all hydroxyl groups.

(11) The granulocyte adsorbent according to (10), wherein the polymer compound is cellulose acetate in which the percentage of hydroxyl groups substituted with acetyl groups is 5% to 53% among all hydroxyl groups.

(12) A system for removing granulocytes used for extracorporeal circulation comprising a device comprising a container containing the granulocyte adsorbent according to any one of (9) to (11), a pump for transporting body fluid, and a pump for injecting an anticoagulant.

(13) A method for producing a granulocyte adsorbent comprising steps of:

(a) obtaining a polymer compound-compound conjugate prepared with a bond of a hydroxyl group of the polymer compound having a plurality of hydroxyl groups and at least one other compound cleavable under alkaline conditions; and (b) cleaving part of a bond between a hydroxyl group of the polymer compound and the other compound by treating the conjugate under alkaline conditions.

(14) The method according to (13), wherein the other compound is carboxylic acid.

(15) The method according to (13) or (14), wherein the polymer compound is polyvinyl alcohol, a polyvinyl alcohol copolymer, or a polysaccharide.

(16) Body fluid or a cell suspension from which granulocytes have been removed, which is prepared by bringing body fluid derived from a mammalian animal or a cell suspension derived therefrom into contact with the granulocyte adsorbent according to any one of (1) to (6).

(17) A method for preparing body fluid or a cell suspension from which granulocytes have been removed comprising steps of:

(a) bringing body fluid obtained from a mammalian animal or a cell suspension derived therefrom into contact with the granulocyte adsorbent according to any one of (1) to (6); and (b) obtaining body fluid or a cell suspension from which granulocytes have been removed.

EFFECTS OF THE INVENTION

With the use of the granulocyte adsorbent according to the present invention, significantly high granulocyte-separating efficiency can be attained, which has heretofore been impossible via conventional techniques.

With the use of the device of the present invention, granulocytes can be effectively and selectively removed from body fluids such as peripheral blood or bone marrow.

The body fluid according to the present invention from which granulocytes have been removed can be used as a cellular source in regenerative medicine, such as in cardiac muscle regeneration or revascularization, or in cellular medicine.

With the utilization of the granulocyte adsorbent of the present invention for extracorporeal circulation, platelet loss can be reduced and granulocytes can be effectively and selectively removed from a body fluid.

This description includes part or all of the contents as disclosed in the descriptions of Japanese Patent Application Nos. 2004-250745 and 2005-91445, which are priority documents of the present application.

PREFERRED EMBODIMENTS OF THE INVENTION

In the present invention, a polymer compound having a plurality of hydroxyl groups may be synthetic or naturally occurring. Examples of polymer compounds having a plurality of hydroxyl groups of the present invention include crosslinked polyvinyl alcohol alone or a crosslinked polyvinyl alcohol and a copolymer of polyvinyl alcohol, such as an ethylene-vinyl alcohol copolymer, a styrene-vinyl alcohol copolymer, an acrylate-vinyl alcohol copolymer, an acrylamide-vinyl alcohol copolymer, and a polysaccharide. Examples of polysaccharides used in the present invention include, but are not limited to, cellulose, sepharose, dextran, agarose, chitin, and chitosan. Preferably, polyvinyl alcohol, an ethylene-vinyl alcohol copolymer, cellulose, chitosan, or the like is used.

In the present invention, "the other compound" can be any compound that reacts with a hydroxyl group of the polymer compound and is capable of forming a polymer compound-compound conjugate. The aforementioned "bond" is preferably cleavable under alkaline conditions, and particularly via contact with a mild alkaline solution. Specific examples of "other compounds" include, but are not limited to: inorganic acid, such as phosphoric acid and sulfuric acid; organic acids, such as saturated or unsaturated, branched or linear, fatty monohydric, dihydric, or polyhydric carboxylic acid, such as formic acid, acetic acid, propionic acid, butyric acid, acrylic acid, methacrylic acid, oleic acid, linolic acid, and linolenic acid; saturated or unsaturated, branched or linear, aromatic monohydric, dihydric, or polyhydric carboxylic acid, such as benzoic acid; amino acid, such as glutamic acid; alcohol, such as saturated or unsaturated, branched or linear, fatty monohydric, dihydric, or polyhydric alcohol, such as methanol, ethanol, 1-propanol, isopropyl alcohol, cyclohexanol, ethylene glycol, and glycerin; and saturated or unsaturated, branched or linear, aromatic monohydric, dihydric, or polyhydric alcohol, such as benzoyl alcohol. Preferably, saturated fatty carboxylic acid, such as formic acid, acetic acid, propionic acid, butyric acid, palmitin acid, stearic acid, or benzoic acid is used.

Reaction between the acid and the polymer compound having a plurality of hydroxyl groups can be realized in the presence of an adequate catalyst, such as sulfuric acid, by the presence of an ester bond. Reaction between the alcohol and the hydroxyl-containing polymer compound can be realized in the presence of an adequate catalyst, such as sulfuric acid, by the presence of an ether bond.

In the present invention, the term "substituent R" refers to any atomic group capable of substituting a hydroxyl group H of the aforementioned hydroxyl-containing polymer compound. Specifically, "substituent R" is deduced to result from the reaction between a hydroxyl group and the "other compound" (typically dehydration) and to be derived from the "other compound." Alternatively, a hydroxyl-protecting group well known in the art may be utilized as substituent R. Such hydroxyl-protecting group is described in, for example, T. H. Greene and P. G. M. Wuts, Protective Groups in Organic Synthesis, vol. 3, John Wiley & Sons, New York, 1999.

Examples of hydroxyl-protecting groups include ether-type, acetal-type, silyl-type, and ester-type protecting groups. The term "ether-type protecting group" refers to a protecting group that forms an ether bond for the purpose of hydroxyl protection. Examples thereof include methyl, ethyl, tert-butyl, octyl, allyl, benzyl, p-methoxymethyl, fluorenyl, trityl, and benzhydryl groups, which have been substituted with a hydroxyl group H. The term "acetal-type protecting group" refers to a protecting group that forms an acetal bond for the purpose of hydroxyl protection. Examples thereof include methoxyethyl, ethoxyethyl, tetrahydropyranyl, and tetrahydrofuranyl. The term "silyl-type protecting group" refers to a protecting group that forms a silyloxy bond for the purpose of hydroxyl protection. Examples thereof include trimethylsilyl, triethylsilyl, tert-butyldimethylsilyl, and tert-butyldiphenylsilyl. The term "ester-type protecting group" refers to a protecting group that forms an ester bond for the purpose of hydroxyl protection. Examples thereof include acetyl, propionyl, isopropionyl, pivaloyl, benzoyl, trifluoroacetyl, and trichloroacetyl groups.

A precursor compound of the hydroxyl-protecting group is included in the scope of "other compounds."

Examples of preferable substituents R include saturated or unsaturated, linear or branched fatty acyl (e.g., alkoxyl carbonyl, acetyl, or oleyl); saturated or unsaturated, linear or branched aromatic acyl (e.g., aryloxycarbonyl, benzoyl, or cinnamoyl), and saturated or unsaturated, linear or branched alkyloxy, alkenyloxy, and alkinyloxy groups. An example of a more preferable substituent R is an aliphatic or aromatic saturated acyl group (e.g., benzoyl), with acetyl being the most preferable. The aforementioned substituent may be substituted with any substituent, such as halogen.

The granulocyte adsorbent of the present invention can be produced by a method comprising steps of (a) obtaining a polymer compound-compound conjugate prepared with a bond of a hydroxyl group having a plurality of hydroxyl groups and at least one other compound of the polymer compound cleavable under alkaline conditions; and (b) cleaving part of a bond between a hydroxyl group of the polymer compound and the other compound by treating the conjugate under alkaline conditions.

Concerning Step (a)

Polymer compound-compound conjugates (e.g., cellulose acetate and polyvinyl acetate) are commercially available. Also, a polymer compound may be allowed to react with the other compound in accordance with a conventional technique to obtain a polymer compound-compound conjugate. For example, an acetylating agent containing acetic anhydride may be added to cellulose obtained from pulp to obtain cellulose acetate. Alternatively, a hydroxyl-containing polymer compound (e.g., cellulose) may be allowed to react with the other compound (e.g., acetic acid) in accordance with a conventional technique to obtain cellulose acetate. Further, a conjugate of a hydroxyl-containing monomer compound and the other compound may be polymerized to obtain the aforementioned conjugate. For example, polyvinyl acetate can be obtained by introducing a mixture comprising monomeric vinyl acetate and triallyl isocyanurate (TAIC) into an aqueous phase comprising water and polyvinyl alcohol, performing thorough agitation mixing and nitrogen substitution in a separable flask equipped with a plate agitation blade and two baffle plates at room temperature, and then performing suspension polymerization while maintaining the internal temperature at 65° C. for 5 hours.

Concerning Step (b)

The polymer compound-compound conjugate comprises a plurality of conjugates of hydroxyl groups of the polymer compound and the other compound. In step (b), the conjugate is treated under mild alkaline conditions to cleave part of the aforementioned plurality of conjugates via, for example, hydrolysis. The degree of cleavage can be adequately adjusted in accordance with the conjugate type and the application of the granulocyte adsorbent. As the granulocyte adsorbent of the present invention, polyvinyl acetate in which preferably 35% to 53%, and more preferably 35% to 49%, of hydroxyl groups have been substituted with acetyl groups among all hydroxyl groups (containing unsubstituted and substituted hydroxyl groups) can be used. As the granulocyte adsorbent of the present invention, cellulose acetate in which preferably 35% to 53%, more preferably 40% to 53%, and further preferably 45% to 51%, of hydroxyl groups have been substituted with acetyl groups among all hydroxyl groups (including unsubstituted and substituted hydroxyl groups) can be used. When the granulocyte adsorbent of the present invention is used for extracorporeal circulation, the percentage of hydroxyl groups substituted with substituents R is preferably 5% to 53%, and more preferably 5% to 50%, among all hydroxyl groups (including unsubstituted and substituted hydroxyl groups) in the polymer compound.

In this description, the "percentage of hydroxyl groups substituted with substituents R among all hydroxyl groups (including unsubstituted and substituted hydroxyl groups) in the polymer compound" may be referred to as the "percentage of hydroxyl groups substituted with substituents R," the "substitution percentage involving substituents R," or simply the "substitution percentage."

The percentage of hydroxyl groups substituted in cellulose acetate with actyl groups can be measured in the following manner, for example. The analyte is thoroughly dried, the dry weight thereof is determined using a precision balance (about 0.5 g), and the analyte is introduced into a flask. A solvent capable of dissolving the analyte (e.g., an aqueous acetone solution, 50 ml) is added, and the mixture is agitated using a stirrer at room temperature for 1 hour. Subsequently, 50 ml of an aqueous solution of 0.2 N sodium hydroxide is added, the mixture is agitated for 5 minutes, and the mixture is then allowed to stand at room temperature for 3 hours. Further, 50 ml of 0.2 N hydrochloric acid is introduced into the flask, the mixture is agitated for 5 minutes, and the resultant is then allowed to stand at room temperature for 1 hour. A few drops of a phenolphthalein solution are introduced into the flask, an aqueous solution of 0.1 N sodium hydroxide is added dropwise thereto using a buret, and the time point at which the color of the solution changes to pale red is designated as the end point to determine the titer (A (ml)). Separately, the same procedure is performed, with the exception that the analyte is not introduced, to determine the titer (B (ml)). Based on such measurements, the percentage of cellulose acetate substituted with acetyl groups can be determined by the following equation.

Substitution percentage=$(A-B)F\times 0.6005$/weight of analyte (g)

F: a factor of an aqueous solution of 0.1 N sodium hydroxide used for titration

Mild alkaline conditions can be realized by a person skilled in the art without undue experimentation.

The percentage of hydroxyl groups in the polymer compounds (e.g., polyvinyl acetate) other than cellulose acetate substituted with substituents R is determined by elementary analysis or analysis based on the infrared absorption spectrum. Alternatively, the saponification percentage may be determined by a conventional technique, and the substitution percentage may be determined by calculating back from the determined saponification percentage (substitution percentage=100−saponification percentage). When the substitution percentage of hydroxyl groups is determined by elementary analysis, an elementary analyzer (Microcorder JM10, J-Science Lab, Co., Ltd.) or the like can be used.

When the polymer compound-compound conjugate obtained in step (a) is a hydroxy-substituted polysaccharide, such as cellulose acetate, partial decomposition in step (b) is preferably carried out under the following conditions. The normality of an alkaline solution is preferably between 0.01 N and 2.0 N, more preferably between 0.05 N and 1 N, and most preferably between 0.07 N to 0.5 N. The reaction time is preferably between 1 minute and 120 minutes, more preferably between 1 minute and 100 minutes, still more preferably between 5 minutes and 60 minutes, and most preferably between 10 minutes and 40 minutes. The reaction temperature is preferably between 10° C. and 90° C., more preferably between 15° C. and 75° C., and most preferably between 20° C. and 58° C.

When the polymer compound-compound conjugate obtained in step (a) is a polyvinyl acetate, partial decomposition in step (b) is preferably carried out under the following conditions. The normality of an alkaline solution is preferably between 0.01 N and 6.0 N, more preferably between 0.1 N and 5.0 N, and most preferably between 1 N to 3.8 N. The reaction time is preferably between 1 minute and 10 hours, more preferably between 30 minutes and 6 hours, and -most preferably between 1 hour and 5.5 hours. The reaction temperature is preferably between 10° C. and 90° C., more preferably between 15° C. and 75° C., and most preferably between 20° C. and 58° C.

An alkaline solution may comprise alcohol, such as methanol, ethanol, or propanol. In such a case, the alcohol content may be at any level between 0.1% (V/V) and 99% (V/V). Such content is preferably between 5% (V/V) and 50% (V/V), and more preferably between 10% (V/V) and 40% (V/V).

According to need, the cleavage product may be purified, following step (b). The method of purification is not particularly limited. For example, purification may be carried out by washing, such as via rinsing.

The granulocyte adsorbent of the present invention is preferably insoluble in water.

In the present invention, the term "body fluid" refers to blood, bone marrow fluid, umbilical cord blood, lymph fluid, diluents thereof, and the like. A cell suspension derived from such body fluid can also be used in the present invention. The term "cell suspension" refers to a fraction prepared by sampling blood, bone marrow fluid, umbilical cord blood, lymph fluid, or the like from a mammalian animal and removing erythrocytes therefrom by specific gravity and density gradient centrifugation, using Ficoll, Percoll, a Vacutainer tube, Lymphoprep, HES (hydroxyethyl starch), or the like (e.g., mononuclear cell fractions or fractions containing cells such as mesenchymal stem cells, hematopoietic stem cells, endothelial precursor cells (EPC), or granulocytes), according to need. The term "cell suspension" also refers to concentrates of these fractions prepared by recentrifugation.

The granulocyte adsorbent of the present invention can be processed into any shape, such as spherical, particulate, flat-membrane, fibrous, or hollow fibrous shapes. When the adsorbent is in a spherical or particulate shape, the average particle diameter is preferably between about 50 μm and 3,000 μm, more preferably between about 80 and 2,000 μm, and most, preferably about 100 and 1,000 μm. The granulocyte adsorbent of the present invention having a spherical or particulate shape can be produced in the following manner, for example. At least one starting monomer compound is dispersed and suspended in a solvent having adequate viscosity, such as water, and the resulting suspension is subjected to polymerization with agitation under adequate conditions to obtain a polymer of a given shape. Alternatively, a polymer is dissolved in a solvent to form drops by the method (oscillation) disclosed in JP Patent Publication (kokai) No. 63-117039 A (1988), and the drops are captured in a coagulation bath for coagulation to obtain a polymer of a given shape. Step (b) can be carried out before and/or after such step.

According to need, the surface of the granulocyte adsorbent of the present invention may be roughened by physical or chemical means.

The surface of the granulocyte adsorbent of the present invention can be of any structure, such as a porous, nonporous, or skin-layer structure. In the case of a porous surface, simultaneously with the adsorption of granulocytes, substances that are not favorable for organisms, such as cytokines produced by other blood cells including granulocytes, enzymes produced upon activation, or eliciting materials may also be removed by adsorption. Pore size is defined in terms of the critical molecular weight for size exclusion. When the granulocyte adsorbent of the present invention is porous, the critical molecular weight for size exclusion is preferably no greater than $1.5\times10^5$, and more preferably no greater than $1.4\times10^5$. If the pore size is greater than $1.4\times10^5$, nonspecific adsorption may be increased, which may result in a loss of useful proteins from body fluid. In order to further reduce the influence of nonspecific adsorption, pores for which the critical molecular weight for size exclusion is no greater than $1.3\times10^5$ are more preferable, molecular weights of no greater than $1.2\times10^5$ are still more preferable, and molecular weights of no greater than $1.0\times10^5$ are most preferable. The term "critical molecular weight for size exclusion" refers to the molecular weight of a molecule that is unable to invade pores at the time of gel-permeation chromatography; that is, the minimal molecular weight at which molecules are excluded, as described in full-fledged textbooks such as "Experimental High-Performance Liquid Chromatography" (Hiroyuki Hatano and Toshihiko Hanai, Kagaku Dojin). In the present invention, porous granulocyte adsorbents are preferably insoluble in water.

The granulocyte adsorbent of the present invention may be used alone or in combination with any hard or soft carriers. For example, the outer surfaces of nuclear carriers can be coated with the granulocyte adsorbent of the present invention. Representative examples of carriers include, but are not limited to: inorganic carriers, such as glass, silica gel, and active carbon carriers; organic carriers comprising synthetic polymers, such as crosslinked polyvinyl alcohol, crosslinked polyacrylate, crosslinked polyacrylamide, and crosslinked polystyrene or polysaccharides such as crosslinked agarose and crosslinked dextrin; cellulose, polyvinyl alcohol, a saponification product of an ethylene-vinyl acetate copolymer, polyacrylamide, polyacrylic acid, polymethacrylic acid, polymethylmethacrylate, polyacrylate-grafted polyethylene, and polyacrylamide-grafted polyethylene, and organic-organic or organic-inorganic composite carriers comprising these substances in combination. The carriers can also have spherical, particulate, flat-membrane, fibrous, or hollow fibrous shapes. When the carriers are of spherical or particulate shapes, the average particle diameter is preferably about 50 µm to 3,000 µm, more preferably about 80 µm to 2,000 µm, and most preferably about 100 µm to 1,000 µm.

When a column is filled with the granulocyte adsorbent of the present invention and used in such state, it is important that clogging does not occur when allowing a liquid to flow through the column. To this end, the granulocyte adsorbent of the present invention is required to have satisfactory mechanical strength. Thus, the granulocyte adsorbent of the present invention is more preferably made of a hard material. In the case of the granulocyte adsorbent of the present invention having a particulate gel form, for example, when the gel evenly fills a cylindrical column and aqueous fluid is allowed to flow into the same, the correlation between pressure loss $\Delta P$ and flow rate is preferably a linear correlation up to about 0.3 kg/cm$^2$, as described in the reference examples below.

The term "granulocytes" used herein refers to, for example, granulocytes in peripheral blood, bone marrow, or umbilical cord blood of mammalian animals, granulocytes in leukocytes concentrated by apheresis, granulocytes in leukocyte fractions isolated by density-gradient centrifugation using Ficoll, a Vacutainer tube, or hydroxyethyl starch (HES), or granulocytes in a cell suspension comprising, suspended in a buffer, a culture solution, physiological saline solution, or leukocyte fractions isolated by any of the aforementioned techniques.

Adsorption of granulocytes using the granulocyte adsorbent of the present invention can be carried out by a variety of techniques. Representative examples of such techniques include the following (1) to (3):

(1) a method wherein body fluid or a cell suspension is brought into contact with the adsorbent by allowing body fluid or a cell suspension to flow through a device comprising an inlet port and an outlet port for body fluid or a cell suspension and a granulocyte adsorbent that fills in a container comprising, mounted at the outlet port, a filter that allows the body fluid or cell suspension to flow therethrough but does not allow the granulocyte adsorbent to flow therethrough;

(2) a method wherein body fluid or a cell suspension is added to a bag containing the granulocyte adsorbent in advance, the body fluid or cell suspension is allowed to react with the granulocyte adsorbent for a given period of time, and the granulocyte adsorbent is then separated by filtration; and (3) a method wherein the granulocyte adsorbent is added to a cell culture system and cells are separated from the granulocyte adsorbent by filtration during or after the completion of culture.

In method (1), a variety of contact methods can be employed. For example, body fluid or a cell suspension is brought into contact under reflux with the granulocyte adsorbent with the aid of a pump for a given period of time, brought into contact without reflux at a given flow rate, or brought into contact without reflux for a given period of time, followed by extrusion at a given flow rate. Contact time is preferably at least 1 minute. For thorough granulocyte adsorption, contact time is more preferably about 3 minutes to 4 hours, still more preferably about 5 minutes to 3 hours, and most preferably about 10 minutes to 2 hours.

Specific examples of method (2) include: a method wherein the sampled body fluid is added to a bag containiwg the granulocyte adsorbent in advance to bring the granulocyte adsorbent into contact with the body fluid; a method wherein a fraction resulting from the removal of erythrocytes from blood by centrifugation or a fraction obtained by further concentrating the same by centrifugation is added to a bag containing the granulocyte adsorbent in advance to bring the granulocyte adsorbent into contact with the fraction; and a method wherein a leukocyte fraction isolated by apharesis and the granulocyte adsorbent are injected into the bag to bring the granulocyte adsorbent into contact with the aforementioned fraction. Contact time is preferably at least 1 minute. For through granulocyte adsorption, contact time is more preferably about 3 minutes to 4 hours, still more preferably about 5 minutes to 3 hours, and most preferably about 10 minutes to 2 hours.

A specific example of method (3) is a method wherein the granulocyte adsorbent is directly added to a system used for culturing a fraction from which erythrocytes have been removed (a cell suspension), which is obtained by removing erythrocytes from body fluid or blood by centrifugation for a given period of time, and after a given period of time, the granulocyte adsorbent is separated from a cell suspension by filtration using a filter that does not allow the granulocyte adsorbent to pass.

Both methods (1) and (2) can be easily performed and are particularly preferable as techniques for removing granulocytes from body fluid or a cell suspension by adsorption. It should be noted that the present invention is not limited thereto.

The present invention also relates to a device comprising a container containing the granulocyte adsorbent. The shape, material, and size of the container used for such device. are not particularly limited. The shape may be spherical, container-shaped, bag-shaped, tubular, columnar, or the like. A specific example of a preferable container is a transparent or semitransparent cylindrical container having a volume of about 0.1 to 500 ml and a diameter of about 0.1 to 10 cm. A container can be prepared from any material. Specific examples of such material include a nonreactive polymer or a metal or alloy having affinity for organisms. Examples of such polymer include an acrylonitrile polymer (e.g., an acrylonitrile butadiene styrene terpolymer), a halogenated polymer (e.g., polytetrafluoroethylene, polychlorotrifluoroethylene, tetrafluoroethylene copolymer, or hexafluoropropylene), polyamide, polysulfone, polycarbonate, polyethylene, polypropylene, polyvinyl chloride-acryl copolymer, polycarbonate acrylonitrile butadiene styrene, and polystyrene. Examples of useful metal materials for the container include stainless steel, titanium, platinum, tantalum, gold, and an alloy of any thereof, gold plated ferroalloy, platinum plated ferroalloy, cobalt chromium alloy, and titanium nitrate-coated stainless steel. Use of a material having sterilization resistance is particularly preferable, and specific examples include silicon-coated glass, polypropylene, vinyl chloride, polycarbonate, polysulfone, and polymethyl pentene.

The device is not limited to the aforementioned. Preferably, the device comprises a container having a liquid inlet, a liquid outlet, and a spill prevention means that allows the body fluid to flow therethrough but does not allow the granulocyte adsorbent to flow therethrough. Also the device preferably comprises the water-insoluble granulocyte adsorbent of the present invention filling or suspended in such container.

Examples of such spill prevention means include mesh, unwoven fabric, and cotton-plug filters.

Use of an anticoagulant is preferable when using the device. Examples of an anticoagulant that can be used include heparin, low-molecular-weight heparin, nafamostat mesilate, gabexate mesilate, argatroban, and a citric-acid-containing anticoagulant, such as an acid-citrate-dextrose (ACD) solution or a citrate-phosphate dextrose (CPD) solution. In general, heparin is particularly preferably used.

The present invention also relates to body fluid or a cell suspension from which granulocytes have been removed, which is prepared by bringing body fluid derived from a mammalian animal or a cell suspension derived therefrom into contact with the granulocyte adsorbent according to the present invention. The body fluid or cell suspension from which granulocytes have been removed can be prepared by a method comprising steps of: (a) bringing body fluid obtained from a mammalian animal or a cell suspension derived therefrom into contact with the granulocyte adsorbent of the present invention; and (b) obtaining body fluid or a cell suspension from which granulocytes have been removed. In step (b), the body fluid or cell suspension can be obtained by any means such as centrifugation, membrane filtration, or chromatography. A person skilled in the art can determine the adequate recovery method based on his/her experimentation or experience.

The concentrations of the cells of interest in the body fluid or cell suspension from which granulocytes have been removed can further be increased by centrifugation. Alternatively, the cells of interest in the body fluid or cell suspension from which granulocytes have been removed by adsorption can be concentrated using, for example, Ficoll, Ficoll-Hypaque, Percoll, a Vacutainer tube, or Lymphoprep.

Cells contained in the body fluid or cell suspension according to the present invention from which granulocytes have been removed can be used for cellular therapy or regenerative medicine. Examples of the purposes of cellular therapy or regenerative medicine include revascularization, cardiac muscle regeneration, bone regeneration, cartilage regeneration, nerve regeneration, and adipose tissue regeneration. The body fluid or cell suspension according to the present invention from which granulocytes have been removed may be used immediately after preparation. Alternatively, it may be refrigerated or cryopreserved followed by thawing.

The body fluid or cell suspension according to the present invention from which granulocytes have been removed may be combined with other pharmaceutically acceptable carriers, excipients, or the like and used as a pharmaceutical composition. Typically, such pharmaceutical composition is directly or transvascularly administered to the affected area by blood transfusion, dripping, injection, or the like. Such pharmaceutical composition can be produced in accordance with acceptable pharmaceutical techniques.

The present invention relates to a method for preventing or treating diseases involving the use of mammalian body fluid or a cell suspension from which granulocytes have been removed, cells for cellular medicine or regenerative medicine prepared therefrom, or the aforementioned pharmaceutical composition. Specific examples of the target diseases to be treated by this method include, but are not limited to, revascularization targeted at vascular occlusion such as occlusive arteriosclerosis or cardiac failure such as myocardial infarct and regeneration of bone, cartilage, alveolodental membrane, or alveolar bone.

The granulocyte adsorbent of the present invention is particularly suitable for ameliorating diseases by selectively removing granulocytes from body fluid by extracorporeal circulation, and typically by blood reflux-based extracorporeal circulation. Examples of diseases treated by this method include, but are not limited to, inflammatory diseases caused by granulocytes, such as ulcerative colitis, Crohn's disease, arthrorheumatism, systemic erythematodes, and Behcet's disease.

The present invention also relates to a system for removing granulocytes used for extracorporeal circulation. The system for removing granulocytes used for extracorporeal circulation according to the present invention comprises at least a device comprising a container containing the granulocyte adsorbent of the present invention, a pump for transporting body fluid, and a pump for injecting an anticoagulant. The device and the anticoagulant are as described above.

A representative example of a method for utilizing the system for removing granulocytes according to the present invention used for extracorporeal circulation is a method wherein body fluid is brought into direct contact with the device described above. For example, such contact may be performed under reflux by maintaining contact between body fluid and the device with the aid of a liquid-transporting pump for a given period of time. For thorough granulocyte adsorption, contact time is preferably at least 1 minute, more preferably between about 3 minutes and 4 hours, further preferably between 5 minutes and 3 hours, and most preferably about 10 minutes to 2 hours.

EXAMPLES

Hereafter, the method of the present invention is described in detail with reference to the following examples.

Example 1

1. Preparation of Granulocyte Adsorbent

Cellulose acetate was dissolved in a mixed solvent comprising dimethyl sulfoxide and propylene glycol, the resulting solution was subjected to droplet formation by the method (oscillation) disclosed in JP Patent Publication (kokai) No. 63-117039 A (1988), and the droplets were coagulated to obtain spherical cellulose acetate particles. The particle diameter of the obtained spherical particles was about 300 μm. The particles were mixed with an aqueous solution of 0.1 N sodium hydroxide at 1:1 (V/V) in terms of sediment volume, and the particles were allowed to react with the aqueous solution for 30 minutes to perform partial hydrolysis. The reaction product was washed with distilled water in an amount approximately 200 times higher than the sediment volume of the adsorbent, and substitution with physiological saline (containing 5 IU/ml of heparin as the final concentration) then took place. The percentage of cellulose acetate substituted with acetyl groups was 49%.

2. Preparation of Rabbit Bone Marrow Fluid

Heparin was added to a phosphate buffer (PBS) to a final concentration of 22 IU/ml, and 6 ml of the resulting solution was introduced into a 50-ml centrifuge tube. Bone marrow fluid (about 20 ml) sampled from the rabbit humeral head (female, 3.5 kg) was added thereto. The bone marrow fluid was filtered through a 70-μm cell strainer to remove blood clots, bone dust, and the like. Thus, the bone marrow fluid of interest was obtained.

3. Conditions for Bone Marrow Fluid—Granulocyte Adsorbent Contact 1 ml of the granulocyte adsorbent of the present invention was measured in terms of sediment volume, the measured adsorbent was transferred to a 5-ml Falcon tube, and physiological saline was removed while avoiding sucking up the granulocyte adsorbent. Immediately thereafter, 2 ml of the bone marrow fluid that had been prepared above was added, and the granulocyte adsorbent was allowed to interact with the bone marrow fluid at 20 rpm (MIX rotor (MIX-ROTAR VMR-5, Iuchi Inc.)) at 37° C. for 1 hour. The supernatant (about 1 ml) was sampled after a given period of time, and the cell count was determined using an automatic blood cell counter (Sysmex K4500). Also, the percentage accounted for by the mononuclear cell fractions and the percentage accounted for by the granulocyte fractions were determined using a flow cytometer (FACSCanto, Becton Dickinson).

As a result, the leukocyte count in the supernatant was 5,100 cells/μl. The percentage accounted for by the leukocyte-constituting granulocyte fractions was found to be 4.0%, and the percentage accounted for by the leukocyte-constituting mononuclear cell fractions (lymphocyte fractions and monocyte fractions) was found to be 84.6%. This demonstrates that the cells in the granulocyte fractions were selectively and remarkably adsorbed by the granulocyte adsorbent.

Example 2

The leukocyte count, the percentage accounted for by the mononuclear cell fractions, and the percentage accounted for by the granulocyte fractions were determined in the same manner as in the case of Example 1, except that the normality of a sodium hydroxide solution was changed to 0.2 N. The percentage of cellulose acetate substituted with acetyl groups was 46%. As a result, the leukocyte count in the supernatant was found to be 6,100 cells/μl. The percentage accounted for by the leukocyte-constituting granulocyte fractions was found to be 9.2%, and the percentage accounted for by the leukocyte-constituting mononuclear cell fractions (lymphocyte fractions and monocyte fractions) was found to be 79.0%. This demonstrates that the cells in the granulocyte fractions were selectively and remarkably adsorbed by the granulocyte adsorbent.

Example 3

A monomer compound (501.6 g) comprising 100 parts by weight of vinyl acetate monomer, 24 parts by weight of triallyl isocyanurate (TAIC), 131.5 parts by weight of ethyl acetate, 48.2 parts by weight of heptane, 12.8 parts by weight of polyvinyl acetate (PVAc) (mean degree of polymerization: 800), and 5.0 parts by weight of 2,2'-azobis(2,4-dimethylvaleronitrile) (V-65) was introduced at room temperature into a 2-l separable flask equipped with a plate agitation blade and two baffle plates comprising 1,045.2 g of an aqueous phase comprising 691.5 parts by weight of water, 0.103 parts by weight of polyvinyl alcohol, 0.023 parts by weight of sodium alpha olefin sulfonate, 5.15 parts by weight of particulate calcium triphosphate (solid content), and 0.039 parts by weight of sodium nitrite. After thorough agitation mixing and nitrogen substitution, the internal temperature was maintained at 65° C. for 5 hours to perform suspension polymerization. After polymerization had been performed for a given period of time, the content of the separable flask was cooled to room temperature. The obtained polymerization slurry was sampled, the weight thereof was measured, a polymerization inhibitor was added to dry a volatile portion in an oven at 120° C., and the constant weight was determined to measure the dry weight. Since the amount of triallyl isocyanurate (TAIC) reduced was minor under such drying conditions, the polymerization conversion rate of vinyl acetate was calculated based on the weights before and after drying, and such rate was found to be 54%.

Subsequently, hydrochloric acid was added to the content of the separable flask, a pH level was adjusted to 2 or lower, and calcium triphosphate was dissolved, followed by thorough washing with water. After the pH level of the wash was adjusted at around neutral, water was substituted with acetone, acetone was added, and the solution was agitated at room temperature for 30 minutes. This extraction washing was repeated twice. Acetone was then substituted with water, and an aqueous solution of sodium hydroxide (NaOH) (determined by the following equation) was added thereto in an excess amount relative to the vinyl acetate unit.

NaOH (solid weight)=dry weight of particles/86.09× 40×1.5

The amount of water was adjusted so as to bring the NaOH concentration to 2% by weight based on water. The solution was held at 30° C. with agitation for 2 hours for partial saponification. The percentage of the polyvinyl acetate substituted with acetyl groups was 41%. Thereafter, washing was continued until the pH level of the wash reached around neutral, hot water was added thereto, and the mixture was agitated at 80° C. for 60 minutes. This process of extraction washing was repeated 4 times. Further, hot water was added thereto in an amount twice the volume of the sediment particles, and extraction was carried out twice in an autoclave at 121° C. for 20 minutes to obtain crosslinked spherical particles. The particle diameter of the obtained polymer particles was about 300 μm. Rabbit bone marrow fluid was brought into contact with the granulocyte adsorbent in the same manner as in the case of Example 1, in order to determine the leukocyte count, the percentage accounted for by the mononuclear cell fractions, and the percentage accounted for by the granulocyte fractions. As a result, the leukocyte count in the supernatant was found to be 6,300 cells/μl. The percentage accounted for by the leukocyte-constituting granulocyte fractions was found to be 19.5%, and the percentage accounted for by the leukocyte-constituting mononuclear cell fractions (lymphocyte fractions and monocyte fractions) was found to be 69.5%. This demonstrates that the cells in the granulocyte fractions were selectively and remarkably adsorbed by the granulocyte adsorbent.

Comparative Example 1

The leukocyte count, the percentage accounted for by the mononuclear cell fractions and the percentage accounted for by the granulocyte fractions were determined in the same manner as in Example 1 except that the normality of a sodium hydroxide solution was changed into 0.4 N. The percentage of cellulose acetate substituted with acetyl groups was 33%. As a result, the leukocyte count in the supernatant was found to be 8,500 cells/μl. The percentage accounted for by the leukocyte-constituting granulocyte fractions was found to be 29.6%, and the percentage accounted for by the leukocyte-constituting mononuclear cell fractions (lymphocyte fractions and monocyte fractions) was found to be 60.2%, which were equivalent to those obtained in Reference Example 1 below.

Comparative Example 2

The leukocyte count, the percentage accounted for by the mononuclear cell fractions, and the percentage accounted for by the granulocyte fractions were determined in the same manner as in Example 1, except that treatment with a sodium hydroxide solution was not carried out. The percentage of cellulose acetate substituted with acetyl groups was 55%. As a result, the leukocyte count in the supernatant was found to be 7,200 cells/µl. The percentage accounted for by the leukocyte-constituting granulocyte fractions was found to be 23.0%, and the percentage accounted for by the leukocyte-constituting mononuclear cell fractions (lymphocyte fractions and monocyte fractions) was found to be 65.6%, which were equivalent to those obtained in Reference Example 1 below.

Comparative Example 3

The leukocyte count, the percentage accounted for by the mononuclear cell fractions, and the percentage accounted for by the granulocyte fractions were determined in the same manner as in Example 1, except that the duration of treatment with sodium hydroxide was changed to 120 minutes. The percentage of cellulose acetate substituted with acetyl groups was found to be 33%. As a result, the leukocyte count in the supernatant was found to be 9,500 cells/µl. The percentage accounted for by the leukocyte-constituting granulocyte fractions was found to be 31.3%, and the percentage accounted for by the leukocyte-constituting mononuclear cell fractions (lymphocyte fractions and monocyte fractions) was found to be 54.9%, which were equivalent to those obtained in Reference Example 1 below.

Reference Example 1

The leukocyte count, the percentage accounted for by the mononuclear cell fractions, and the percentage accounted for by the granulocyte fractions were determined in the same manner as in Example 1, except that rabbit bone marrow fluid that had not been brought into contact with the granulocyte adsorbent was used. As a result, the leukocyte count in the supernatant was found to be 10,200 cells/µl. The percentage accounted for by the leukocyte-constituting granulocyte fractions was found to be 30.9%, and the percentage accounted for by the leukocyte-constituting mononuclear cell fractions (lymphocyte fractions and monocyte fractions) was found to be 56.2%.

The leukocyte count, the percentage accounted for by the leukocyte-constituting granulocyte fractions, and the percentage accounted for by the leukocyte-constituting mononuclear cell fractions (lymphocyte fractions and monocyte fractions) of Examples 1 to 3, Comparative Examples 1 to 3, and Reference Example 1 are summarized in Table 1.

TABLE 1

Leukocyte count and percentages of cell fractions after contact with adsorbent

| | Leukocyte count (×100 cells/µl) | Mononuclear cell fraction (%) | Granulocyte fraction (%) |
| --- | --- | --- | --- |
| Ex. 1 | 51 | 84.6 | 4.0 |
| Ex. 2 | 61 | 79.0 | 9.2 |
| Ex. 3 | 63 | 69.5 | 19.5 |
| Comp. Ex. 1 | 85 | 60.2 | 29.6 |
| Comp. Ex. 2 | 72 | 65.6 | 23.0 |
| Comp. Ex. 3 | 95 | 54.9 | 31.3 |
| Ref. Ex. 1 | 102 | 56.2 | 30.9 |

Example 4

The leukocyte count, the percentage accounted for by the mononuclear cell fractions, and the percentage accounted for by the granulocyte fractions were determined in the same manner as in Example 1, except that a mixed solvent prepared by adjusting the final normality of sodium hydroxide to 0.2N (5:95 (distilled water:ethanol) was used. The percentage of cellulose acetate substituted with acetyl groups was found to be 44%. As a result, the leukocyte count in the supernatant was found to be 3,800 cells/µl. The percentage accounted for by the leukocyte-constituting granulocyte fractions was found to be 5.5%, and the percentage accounted for by the leukocyte-constituting mononuclear cell fractions (lymphocyte fractions and monocyte fractions) was found to be 85.8%. This demonstrates that the cells in the granulocyte fractions were selectively and remarkably adsorbed by the granulocyte adsorbent.

Comparative Example 4

Spherical particles were produced in the same manner as in example 1, except that the starting material of the granulocyte adsorbent was changed to polymethyl methacrylate (PMMA) and that alkaline treatment was not carried out. The particle diameter of the obtained spherical PMMA particles was about 300 µm. Rabbit bone marrow fluid was brought into contact with the granulocyte adsorbent in the same manner as in Example 1, in order to determine the leukocyte count, the percentage accounted for by the mononuclear cell fractions, and the percentage accounted for by the granulocyte fractions. As a result, the leukocyte count in the supernatant was found to be 5,300 cells/µl. The percentage accounted for by the leukocyte-constituting granulocyte fractions was found to be 37.7%, and the percentage accounted for by the leukocyte-constituting mononuclear cell fractions (lymphocyte fractions and monocyte fractions) was found to be 54.6%, which were equivalent to those obtained in Reference Example 2 below.

Comparative Example 5

Spherical particles were produced in the same manner as in example 1, except that the starting material of the granulocyte adsorbent was changed to polyacrylonitrile (PAN) and that alkaline treatment was not carried out. The particle diameter of the obtained spherical PAN particles was about 300 µm. Rabbit bone marrow fluid was brought into contact with the granulocyte adsorbent in the same manner as in Example 1, in order to determine the leukocyte count, the percentage accounted for by the mononuclear cell fractions, and the percentage accounted for by the granulocyte fractions. As a result, the leukocyte count in the supernatant was found to be 5,600 cells/µl. The percentage accounted for by the leukocyte-constituting granulocyte fractions was found to be 36.4%, and the percentage accounted for by the leukocyte-constituting mononuclear cell fractions (lymphocyte fractions and monocyte fractions) was found to be 54.1%, which were equivalent to those obtained in Reference Example 2 below.

Comparative Example 6

Spherical particles were produced in the same manner as in example 1, except that the starting material of the granulocyte adsorbent was changed to polystyrene (PSt) and that alkaline treatment was not carried out. The particle diameter of the obtained spherical PSt particles was. about 300 µm. Rabbit bone marrow fluid was brought into contact with the granulocyte adsorbent in the same manner as in Example 1, in order to determine the leukocyte count, the percentage accounted for by the mononuclear cell fractions, and the percentage accounted for by the granulocyte fractions. As a result, the leukocyte count in the supernatant was found to be 5,100 cells/μl. The percentage accounted for by the leukocyte-constituting granulocyte fractions was found to be 38.3%, and the percentage accounted for by the leukocyte-constituting mononuclear cell fractions (lymphocyte fractions and monocyte fractions) was found to be 53.7%, which were equivalent to those obtained in Reference Example 2 below.

Comparative Example 7

Spherical particles were produced in the same manner as in example 1, except that the starting material of the granulocyte adsorbent was changed to polysulfone (PS) and that alkaline treatment was not carried out. The particle diameter of the obtained spherical PS particles was about 300 μm. Rabbit bone marrow fluid was brought into contact with the granulocyte adsorbent in the same manner as in Example 1, in order to determine the leukocyte count, the percentage accounted for by the mononuclear cell fractions, and the percentage accounted for by the granulocyte fractions. As a result, the leukocyte count in the supernatant was found to be 5,800 cells/μl. The percentage accounted for by the leukocyte-constituting granulocyte fractions was found to be 37.1%, and the percentage accounted for by the leukocyte-constituting mononuclear cell fractions (lymphocyte fractions and monocyte fractions) was found to be 54.1%, which were equivalent to those obtained in Reference Example 2 below.

Reference Example 2

The leukocyte count, the percentage accounted for by the mononuclear cell fractions, and the percentage accounted for by the granulocyte fractions were determined in the same manner as in Example 1, except for the use of rabbit bone marrow fluid that had not been brought into contact with the granulocyte adsorbent. As a result, the leukocyte count in the supernatant was found to be 6,300 cells/μl. The percentage accounted for by the leukocyte-constituting granulocyte fractions was found to be 37.8%, and the percentage accounted for by the leukocyte-constituting mononuclear cell fractions (lymphocyte fractions and monocyte fractions) was found to be 54.7%.

The leukocyte count, the percentage accounted for by the leukocyte-constituting granulocyte fractions, and the percentage accounted for by the leukocyte-constituting mononuclear cell fractions (lymphocyte fractions and monocyte fractions) of Example 4, Comparative Examples 4 to 7, and Reference Example 2 are summarized in Table 2.

TABLE 2

Leukocyte count and percentages of cell fractions after contact with adsorbent

| | Leukocyte count (×100 cells/μl) | Mononuclear cell fraction (%) | Granulocyte fraction (%) |
|---|---|---|---|
| Ex. 4 | 38 | 85.8 | 5.5 |
| Comp. Ex. 4 | 53 | 54.6 | 37.7 |
| Comp. Ex. 5 | 56 | 54.1 | 36.4 |
| Comp. Ex. 6 | 51 | 53.7 | 38.3 |
| Comp. Ex. 7 | 58 | 54.1 | 37.1 |
| Ref. Ex. 2 | 63 | 54.7 | 37.8 |

Example 5

1. Preparation of Granulocyte Adsorbent

Cellulose acetate was dissolved in a mixed solvent comprising dimethyl sulfoxide and propylene glycol, the resulting solution was subjected to droplet formation by the method (oscillation) disclosed in JP Patent Publication (kokai) No. 63-117039 A (1988), and the droplets were coagulated to obtain spherical cellulose acetate particles. The particle diameter of the obtained spherical particle was about 300 μm. The particles were mixed with an aqueous solution of 0.1 N sodium hydroxide at 1:1 (V/V) in terms of sediment volume, and the particles were allowed to react with the aqueous solution for 30 minutes to perform partial hydrolysis. The reaction product was washed with distilled water in an amount approximately 200 times the volume of the sediment adsorbent and then substituted with physiological saline (containing 5 IU/ml of heparin as the final concentration). The percentage of cellulose acetate substituted with acetyl groups was 49%.

2. Conditions for Blood—Granulocyte Adsorption Column Contact

The obtained adsorbent was washed with heparin-containing physiological saline (heparin sodium injection, Yoshitomi Seiyaku Co. Ltd.) (physiological saline was adjusted to contain heparin at a final concentration of 5 IU/ml), and heparin was equilibrated. Subsequently, carriers were subjected to degassing, and 3.0 ml thereof in terms of sediment volume was filled in a mini column (acrylic column; inner diameter: 10 mm; height: 38 mm). A polyvinyl chloride tube (inner diameter: 1 mm; outer diameter: 3 mm; length: 70 cm) was mounted on the column inlet side, and a similar polyvinyl chloride tube (length: 30 cm) was mounted on the column outlet side. Blood was sampled from healthy volunteers using 18 G injection needles through the brachial region with caution. Heparin was used as an anticoagulant, and the heparin concentration in the blood was adjusted at 5 IU/ml. The blood (40 ml) to which an anticoagulant had been added was introduced into a Teflon® triangular flask (internal volume: 50 ml; Sanwa), the flask was allowed to stand in an incubator at 37° C., and the flask was mildly agitated once every 5 minutes. Subsequently, a blood flow experiment was initiated at a flow rate of 0.5 ml/min. The time point at which blood came out of the column outlet was determined as the initiation point, the outlet end of the tube was returned to the blood pool, and a reflux experiment was carried out for 120 minutes. Blood was sampled from the column outlet 30 minutes, 60 minutes, and 120 minutes after the initiation.

[Measurement of Blood Cell Count]

After a given period of time, blood was sampled from the column outlet. The blood cell counts (erythrocytes, leukocytes, and platelets) were measured using a blood cell counter (K-4500, Sysmex). The results are shown in Table 3. Also, the percentage accounted for by the mononuclear cell fractions (lymphocytes and monocytes) and the percentage accounted for by the granulocyte fractions were determined using a flow cytometer (FACSCanto, Becton Dickinson). The results are shown in Table 4.

As a result, the leukocyte count on the column outlet side was found to be about 1,500 cells/μl on average. When an empty column containing no adsorbing material was used (Reference Example 3), however, the leukocyte count was about 6,500 cells/μl on average. Thus, the leukocyte count on the column outlet side remarkably decreased in the examples of the present invention. Significant change was not observed concerning erythrocytes and platelets in comparison with Reference Examples (Table 3). The percentage accounted for by the leukocyte-constituting granulocyte fractions was found to be about 63%, and the percentage accounted for by the leukocyte-constituting mononuclear cell fractions (lymphocyte fractions and monocyte fractions) was found to be about 35%, when an empty column containing no adsorbent was used (Reference Example 3). After flowing through a column, the percentage of mononuclear cell fractions was about 96%, and the percentage of granulocyte fractions was about 3%. This demonstrates that the granulocytes were selectively and remarkably adsorbed by the granulocyte adsorbent (Table 4).

Example 6

The blood cell count, the percentage accounted for by the mononuclear cell fractions, and the percentage accounted for by the granulocyte fractions were determined in the same manner as in the case of Example 5, except that the normality of a sodium hydroxide solution was changed to 0.2 N. The percentage of cellulose acetate substituted with acetyl groups was 46%. As a result, the leukocyte count on the column outlet side was found to be about 1,900 cells/lil on average, which was significantly decreased compared with Reference Example 3. Substantially no change was observed concerning erythrocytes and platelets (Table 3). The percentage accounted for by the leukocyte-constituting granulocyte fractions was found to be about 9%, and the percentage accounted for by the leukocyte-constituting mononuclear cell fractions (lymphocyte fractions and monocyte fractions) was found to be about 90%. This demonstrates that the granulocytes were selectively and remarkably adsorbed by the adsorbent compared with Reference Example 3 (Table 4).

Example 7

Cellulose acetate was dissolved in a mixed solvent comprising dimethyl sulfoxide and propylene glycol, the resulting solution was subjected to droplet formation by the method (oscillation) disclosed in JP Patent Publication (kokai) No. 63-117039 A (1988), and the droplets were coagulated to obtain spherical cellulose acetate particles. The particle diameter of the obtained spherical particles was about 500 μm. The particles were subjected to alkaline treatment in the same manner as in Example 5 (the percentage of cellulose acetate substituted with acetyl groups was found to be 48.6%), in order to determine the blood cell count, the percentage accounted for by the mononuclear cell fractions, and the percentage accounted for by the granulocyte fractions. As a result, the leukocyte count on the column outlet side was found to be about 2,200 cells/μl on average, which was significantly decreased compared with Reference Example 3. No substantial change was observed concerning erythrocytes and platelets (Table 3). The percentage accounted for by the leukocyte-constituting granulocyte fractions was found to be about 10%, and the percentage accounted for by the leukocyte-constituting mononuclear cell fractions (lymphocyte fractions and monocyte fractions) was found to be about 87%. This demonstrates that the granulocytes were selectively and remarkably adsorbed by the adsorbent compared with Reference Example 3 (Table 4).

Example 8

The blood cell count, the percentage accounted for by the mononuclear cell fractions, and the percentage accounted for by the granulocyte fractions were determined in the same manner as in the case of Example 5, except for the use of the spherical polyvinyl acetate particles prepared in Example 3. As a result, the leukocyte count on the column outlet side was about 2,200 cells/μl on average, which was significantly decreased compared with Reference Example 3. No substantial change was observed concerning erythrocytes and platelets (Table 3). The percentage accounted for by the leukocyte-constituting granulocyte fractions was found to be about 9%, and the percentage accounted for by the leukocyte-constituting mononuclear cell fractions (lymphocyte fractions and monocyte fractions) was found to be about 90%. This demonstrates that the granulocytes were selectively and remarkably adsorbed by the adsorbent compared with Reference Example 3 (Table 4).

Comparative Example 8

The leukocyte count, the percentage accounted for by the mononuclear cell fractions, and the percentage accounted for by the granulocyte fractions were determined in the same manner as in Example 5, except that treatment with a sodium hydroxide solution was not carried out. The percentage of cellulose acetate substituted with acetyl groups was found to be 54.0%. As a result, the leukocyte count on the column outlet side was about 3,700 cells/μl on average. No change was observed concerning the erythrocyte count; however, the platelet count decreased compared with Examples (Table 3). The percentage accounted for by the leukocyte-constituting granulocyte fractions was found to be about 25%, and the percentage accounted for by the leukocyte-constituting mononuclear cell fractions (lymphocyte fractions and monocyte fractions) was found to be about 71%. This demonstrates that the granulocytes were selectively adsorbed by the adsorbent compared with Reference Example 3, although the degree of adsorption did not reach that of the examples above (Table 4).

Comparative Example 9

The leukocyte count, the percentage accounted for by the mononuclear cell fractions, and the percentage accounted for by the granulocyte fractions were determined in the same manner as in Example 5, except that the particles obtained in Example 8 were not treated with sodium hydroxide (not subjected to saponification). The percentage of the polyvinyl acetate substituted, with acetyl groups was 55%. As a result, the leukocyte count on the column outlet side was about 3,500 cells/μl on average. No change was observed concerning the erythrocyte count; however, the platelet count decreased compared with Examples (Table 3). The percentage accounted for by the leukocyte-constituting granulocyte fractions was found to be about 52%, and the percentage accounted for by the leukocyte-constituting mononuclear cell fractions (lymphocyte fractions and monocyte fractions) was found to be about 44%. This demonstrates that granulocyte selectivity was not substantially observed (Table 4).

Comparative Example 10

Spherical PVA particles were produced in the same manner as in Example 8, except that the saponification was carried out at an NaOH concentration of 4% by weight at 40° C. for 6 hours. The percentage of cellulose acetate substituted with acetyl groups was found to be 4%. The particle diameter was about 300 μm. Blood was brought into contact with the granulocyte adsorbent in the same manner as in Example 5, in order to determine the leukocyte count, the percentage accounted for by the mononuclear cell fractions, and the percentage accounted for by the granulocyte fractions. As a result, the leukocyte count on the column outlet side was found to be about 5,700 cells/μl on average. No change was observed concerning the erythrocyte count; however, the platelet count decreased compared with Examples (Table 3). The percentage accounted for by the leukocyte-constituting granulocyte fractions was found to be 65%, and the percentage accounted for by the leukocyte-constituting mononuclear cell fractions (lymphocyte fractions and monocyte fractions) was found to be 31%, which were equivalent to those obtained in Reference Example 3 (Table 4).

Comparative Example 11

The leukocyte count, the percentage accounted for by the mononuclear cell fractions, and the percentage accounted for by the granulocyte fractions were determined in the same manner as in example 5, except that the starting material of the particles was changed to polymethyl methacrylate (PMMA) and that alkaline treatment was not carried out. As a result, the leukocyte count on the column outlet side was about 5,600 cells/μl on average. No change was observed concerning the erythrocyte count; however, the platelet count decreased compared with Examples (Table 3). The percentage accounted for by the leukocyte-constituting granulocyte fractions was found to be about 65%, and the percentage accounted for by the leukocyte-constituting mononuclear cell fractions (lymphocyte fractions and monocyte fractions) was found to be about 31%, which were equivalent to those obtained in Reference Example 3 (Table 4).

Comparative Example 12

The leukocyte count, the percentage accounted for by the mononuclear cell fractions, and the percentage accounted for by the granulocyte fractions were determined in the same manner as in Example 5, except that the starting material of the granulocyte adsorbent was changed to polystyrene (PSt) and that alkaline treatment was not carried out. As a result, the leukocyte count on the column outlet side was about 5,200 cells/μl on average. No change was observed concerning the erythrocyte count; however, a decrease in the platelet count was significant (Table 3). The percentage accounted for by the leukocyte-constituting granulocyte fractions was found to be about 63%, and the percentage accounted for by the leukocyte-constituting mononuclear cell fractions (lymphocyte fractions and monocyte fractions) was found to be about 32%, which were equivalent to those obtained in Reference Example 3 (Table 4).

Reference Example 3

The leukocyte count, the percentage accounted for by the mononuclear cell fractions, and the percentage accounted for by the granulocyte fractions were determined in the same manner as in Example 5, except for the use of a column containing no particles. As a result, the leukocyte count on the column outlet side was found to be about 6,500 cells/μl on average. No change was observed concerning the erythrocyte count; however, a decrease in the platelet count was significant (Table 3). The percentage accounted for by the leuko-cyte-constituting granulocyte fractions was found to be about 63%, and the percentage accounted for by the leukocyte-constituting mononuclear cell fractions (lymphocyte fractions and monocyte fractions) was found to be about 35% (Table 4).

Thus, use of the granulocyte adsorbent and the system for removing granulocytes of the present invention was found to enable efficient and selective removal of granulocytes from body fluid while reducing platelet loss by direct blood reflux-based extracorporeal circulation.

The blood cell counts of the column outlet at each time point of Examples 5 to 8, Comparative Examples 8 to 12, and Reference Example 3 are summarized in Table 3. Also, the percentage accounted for by the leukocyte-constituting granulocyte fractions and the percentage accounted for by the leukocyte-constituting mononuclear cell fractions (the lymphocyte fractions and monocyte fractions) are summarized in Table 4.

TABLE 3

| | Blood cell concentration on column outlet side | | | |
|---|---|---|---|---|
| | Blood cell type | 30 min | 60 min | 120 min |
| Ex. 5 | Erythrocytes | 522 | 518 | 513 |
| | Leukocytes | 15 | 16 | 15 |
| | Platelets | 20.1 | 17.6 | 16.8 |
| Ex. 6 | Erythrocytes | 513 | 518 | 528 |
| | Leukocytes | 20 | 18 | 19 |
| | Platelets | 22.3 | 18.8 | 17.4 |
| Ex. 7 | Erythrocytes | 521 | 516 | 518 |
| | Leukocytes | 22 | 24 | 21 |
| | Platelets | 21.7 | 19.8 | 18.6 |
| Ex. 8 | Erythrocytes | 520 | 516 | 519 |
| | Leukocytes | 23 | 22 | 20 |
| | Platelets | 20.8 | 18.7 | 18.5 |
| Comp. Ex. 8 | Erythrocytes | 508 | 511 | 519 |
| | Leukocytes | 39 | 37 | 36 |
| | Platelets | 18.6 | 16.6 | 15.3 |
| Comp. Ex. 9 | Erythrocytes | 517 | 522 | 514 |
| | Leukocytes | 37 | 34 | 35 |
| | Platelets | 17.8 | 16.3 | 14.3 |
| Comp. Ex. 10 | Erythrocytes | 509 | 526 | 518 |
| | Leukocytes | 58 | 57 | 56 |
| | Platelets | 16.4 | 15.1 | 13.8 |
| Comp. Ex. 11 | Erythrocytes | 506 | 515 | 513 |
| | Leukocytes | 57 | 56 | 54 |
| | Platelets | 15.6 | 13.4 | 12.7 |
| Comp. Ex. 12 | Erythrocytes | 524 | 504 | 515 |
| | Leukocytes | 55 | 52 | 49 |
| | Platelets | 8.9 | 5.5 | 4.3 |
| Ref. Ex. 3 | Erythrocytes | 512 | 508 | 521 |
| | Leukocytes | 67 | 65 | 64 |
| | Platelets | 23.3 | 22.1 | 21.8 |

Unit: erythrocytes and platelets: 10,000 cells/μl; Leukocytes: 100 cells/μl

TABLE 4

| | Percentages of Leukocytes fractions on column outlet side (unit: %) | | | | | |
|---|---|---|---|---|---|---|
| | Circulation time | | | | | |
| | 30 min | | 60 min | | 120 min | |
| | Mononuclear cell fraction | Granulocyte fraction | Mononuclear cell fraction | Granulocyte fraction | Mononuclear cell fraction | Granulocyte fraction |
| Ex. 5 | 95.3 | 3.1 | 96.1 | 2.8 | 96.3 | 2.9 |
| Ex. 6 | 87.9 | 9.3 | 91.2 | 8.7 | 90.8 | 8.2 |
| Ex. 7 | 84.6 | 10.3 | 89.2 | 9.8 | 88.5 | 9.3 |
| Ex. 8 | 87.4 | 8.8 | 90.3 | 9.4 | 91.3 | 9.5 |
| Comp. Ex. 8 | 70.9 | 25.7 | 70.2 | 25.3 | 71.5 | 23.4 |
| Comp. Ex. 9 | 43.5 | 52.6 | 45.2 | 50.5 | 44.6 | 51.4 |
| Comp. Ex. 10 | 32.1 | 64.8 | 32.2 | 64.4 | 29.8 | 66.3 |
| Comp. Ex. 11 | 30.7 | 63.5 | 30.2 | 65.7 | 32.4 | 64.5 |
| Comp. Ex. 12 | 32.1 | 62.6 | 31.4 | 61.8 | 32.3 | 65.2 |
| Ref. Ex. 3 | 35.1 | 62.9 | 33.9 | 64.3 | 35.1 | 62.1 |

All publications, patents, and patent applications cited herein are incorporated herein by reference in their entirety.

The invention claimed is:

1. A granulocyte adsorbent comprising a polymer compound having an unsubstituted hydroxyl group and a hydroxyl group in which H has been substituted with acetyl, wherein the polymer compound is at least one selected from
    cellulose acetate in which the percentage of hydroxyl groups substituted with acetyl groups is 44% to 51% among all hydroxyl groups, and
    polyvinyl acetate in which the percentage of hydroxyl groups substituted with acetyl groups is 35% to 49% among all hydroxyl groups.

2. The granulocyte adsorbent according to claim 1, which is insoluble in water.

3. A device comprising a container that contains the granulocyte adsorbent according to claim 1.

4. The device according to claim 3, wherein the container comprises an inlet and an outlet for liquid.

5. The granulocyte adsorbent according to claim 1 used for extracorporeal circulation.

6. A system for removing granulocytes used for extracorporeal circulation comprising a device comprising a container containing the granulocyte adsorbent according to claim 5, a pump for transporting body fluid, and a pump for injecting an anticoagulant.

7. A method for producing a granulocyte adsorbent comprising steps of:
    (a) obtaining polyvinyl acetate; and
    (b) cleaving part of acetyl groups of said polyvinyl acetate by treating said polyvinyl acetate under alkaline conditions,
    wherein said polyvinyl acetate has an unsubstituted hydroxyl group and a hydroxyl group in which H has been substituted with acetyl, wherein the percentage of hydroxyl groups substituted with acetyl groups in said polyvinyl acetate is 35% to 49% among all hydroxyl groups.

8. A method for preparing body fluid or a cell suspension from which granulocytes have been removed comprising steps of:
    (a) bringing body fluid obtained from a mammalian animal or a cell suspension derived therefrom into contact with the granulocyte adsorbent according to claim 1; and
    (b) obtaining body fluid or a cell suspension from which granulocytes have been removed.

* * * * *